United States Patent
Elgas et al.

[11] Patent Number: 5,922,281
[45] Date of Patent: *Jul. 13, 1999

[54] SURFACE TREATMENT FOR MICRO-CONDUITS EMPLOYED IN BLOOD HEAT EXCHANGE SYSTEM

[75] Inventors: Roger J. Elgas, Anaheim Hills; Robert F. Gremel, Huntington Beach; Henry W. Palermo, Burbank; Richard Larson Bringham, San Clemente, all of Calif.

[73] Assignee: Medtronic, Inc., Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/585,323

[22] Filed: Jan. 11, 1996

[51] Int. Cl.$^6$ ........................................... A61M 1/14
[52] U.S. Cl. ...................... 422/45; 422/44; 261/DIG. 28
[58] Field of Search ................................ 422/44, 45, 46; 261/DIG. 28

[56] References Cited

U.S. PATENT DOCUMENTS

| | | | |
|---|---|---|---|
| 3,697,635 | 10/1972 | Dietzch et al. | 264/135 |
| 4,265,276 | 5/1981 | Hatada et al. | 138/177 |
| 4,329,229 | 5/1982 | Bodnar et al. | 210/321.2 |
| 4,554,076 | 11/1985 | Speaker | 210/639 |
| 4,975,247 | 12/1990 | Badolato et al. | 422/48 |
| 5,211,913 | 5/1993 | Hagiwara et al. | 422/44 |
| 5,270,004 | 12/1993 | Cosentino et al. | 422/46 |

FOREIGN PATENT DOCUMENTS

| | | | |
|---|---|---|---|
| 60172309 | 9/1985 | European Pat. Off. | B01D 13/04 |
| 0299381A2 | 1/1989 | European Pat. Off. | A61M 1/18 |
| 0381757A1 | 8/1990 | European Pat. Off. | A61L 33/00 |
| 3712491A1 | 10/1987 | Germany | B01D 13/00 |

OTHER PUBLICATIONS

Maxima Hollow Fiber Membrane Oxygenator—four page brochure (undated).
Minimax Plus Oxygenation Systems—five page brochure (undated).

*Primary Examiner*—Robert J. Warden
*Assistant Examiner*—Fariborz Moazzam
*Attorney, Agent, or Firm*—Michael H. Jester

[57] ABSTRACT

Blood heat exchanger apparatus with improved heat exchanged capability and improved bonding of micro-conduit heat exchange fibers. The micro-conduit comprises a plurality of elongated fibers, which may be made of a hydrophobic material such as polypropylene or polyethylene. The micro-conduit fibers may be provided as a heat exchanger micro-conduit wrapping material, wherein the micro-conduit fibers are attached to a thin flexible interconnect, such as woven netting, to maintain the fibers at predetermined and substantially parallel alignment with each other. The wrapping material is wrapped about an elongated spindle to provide a generally cylindrical heat exchange core. A shell is placed around the core to contain the heat transfer fluid which passes around the exterior of the fibers. Opposing first and second seals are created by applying potting compound between fibers proximate the spindle's first and second ends respectively. The surface chemistry of the fibers is modified by a treatment such as corona treatment process to facilitate bonding of the seals which comprises a potting compound such as urethane.

15 Claims, 4 Drawing Sheets

SURFACE TREATMENT FOR MICRO-CONDUITS EMPLOYED IN BLOOD HEAT EXCHANGE SYSTEM

BACKGROUND OF THE INVENTION

1. Field of the Invention

The present invention generally relates to heat exchangers for use in regulating the temperature of a patient's blood during surgery, and more particularly to a micro-conduit heat exchanger with enhanced sealing between the heat transfer fluid and the patient's blood.

2. Description of the Related Art

"Heart-lung" machines are known in the medical field. One component of these machines is a blood oxygenator. Blood oxygenators are typically disposable and serve to infuse oxygen into a patient's blood during medical procedures such as heart surgery. Most commercially available blood oxygenators employ a membrane-type oxygenator, which comprises thousands of tiny hollow fibers having microscopic pores. Inside the membrane oxygenator blood flows around the outside surfaces of these fibers while a controlled oxygen-rich gas mixture is pumped through the fibers. Due to the relatively high concentration of carbon dioxide in the blood arriving from the patient, carbon dioxide from the blood diffuses through the fibers' microscopic pores and into the gas mixture. Due to the relatively low concentration of oxygen in the blood arriving from the patient, oxygen from the gas mixture diffuses into the blood through the fibers' microscopic pores.

Most blood oxygenators also employ a heat exchanger to precisely regulate the temperature of a patient's blood. The heat exchanger usually includes one or more relatively large conduits housed in a vessel. The patient's blood is continuously pumped through the conduits, while a heat transfer fluid such as water flows through the vessel around the conduits, or vice versa. The heat exchange medium is either heated or cooled to maintain the patient's blood at a desired temperature.

One example of a commercially successful blood oxygenator is sold under the designation MAXIMA™ by Medtronic Corp. In the MAXIMA blood oxygenator, the heat transfer fluid (water) flows inside relatively large diameter metal tubes while blood flows on the outside of the tubes within the vessel. The TERUMO brand oxygenator uses a different configuration, where blood flows inside relatively large diameter metal tubes. In the BARD WILLIAM HARVEY HF-5700 blood oxygenator, the blood flows outside plastic tubes that contain a flow of temperature-regulated water.

Heat exchangers in blood oxygenators are subject to a number of design constraints. The heat exchangers should be compact due to physical space limitations in the operating room environment. Also, small size is important in minimizing the internal priming volume of the blood oxygenator due to the high cost and limited supply of blood. However, the heat exchanger must be large enough to provide an adequate volumetric flow rate to allow proper temperature control and oxygenation. On the other hand, blood flow rate or flow resistance inside the blood oxygenator must not be excessive since the cells and platelets in the human blood are delicate and can be traumatized if subjected to excessive shear forces resulting from turbulent flow.

One way to meet the above requirements is to provide a heat exchanger with improved heat exchange efficiency. A more efficient heat exchanger can provide adequate temperature control in a compact space with minimal priming volume. Some improvement in heat exchange efficiency may be achieved by the use of certain heat transfer fluids. However, because of toxicity considerations, blood oxygenator heat exchangers generally utilize water as a heat transfer fluid.

Another way to increase the heat exchange efficiency is to increase the surface area of contact between the blood and the heat transfer fluid. While this can be done by simply enlarging the heat exchanger, the above considerations severely limit the size of the heat exchanger to relatively small proportions. Another approach would be to increase the number of heat exchanger conduits while decreasing their size. This would result in increased surface area contact with the blood while maintaining a small volume.

However, a number of problems can be encountered with smaller heat exchanger conduits. For example, finding an appropriate material for the heat exchanger tubes is difficult. Many materials are not suitable for this application due to the extremely low tolerance of contamination and toxicity. While metals have been successfully used in past blood heat exchangers, metals present a number of difficulties. First, since metal tubes of small diameter must be manufactured more precisely, they are more expensive than larger tubes. Furthermore, this expense is compounded due to the increased number of heat exchanger tubes required in such a design.

Plastic materials, while less expensive than metals to manufacture in small sizes, pose different problems when used for heat exchanger conduits. Plastics have poor heat transfer characteristics, and therefore, their use necessitates an even greater surface area to efficiently achieve a desired rate of heat exchange. Moreover, many desirable plastic materials can pose problems due to their relatively low critical surface tension. As a result, plastic materials do not "wet" easily which also makes it difficult to "prime" the interior of the conduits before injecting blood into them to avoid air bubbles in the conduits. This also causes difficulties in reliably bonding to these materials. Bonding to blood heat exchanger conduits is critical to ensure that there is absolute isolation of the heat transfer fluid from the blood. Furthermore, the bonding material must be non-toxic and biocompatible since it will likely be in contact with the blood.

SUMMARY OF THE INVENTION

It is therefore an object of the present invention to provide an improved blood heat exchanger.

It is another object of the present invention to minimize the size of a blood heat exchanger.

It is another object of the present invention to provide a blood heat exchanger which has improved heat transfer characteristics.

It is another object of the present invention to provide a blood heat exchanger which utilizes small size polymeric conduits and which effectively and reliably seals the heat transfer fluid from the blood.

In accordance with the present invention, a blood heat exchange system generally comprises a plurality of small polymeric hollow conduits for conveying blood. A heat transfer fluid flow path conveys a heat transfer fluid around the outside surfaces of the hollow conduits. An inlet chamber directs blood into the hollow conduits and an outlet chamber receives blood leaving the hollow conduits. The hollow conduits are generally arranged in a bundle, each conduit having a first end terminating in the inlet chamber and a second end terminating in the outlet chamber. Each end of the conduit bundle is embedded in one of two sealing members which seal the inlet and output chambers respectively from the heat transfer fluid flow path disposed therebetween. To ensure a reliable seal between the heat transfer flow path and the inlet and output chambers, at least the end portions of the hollow conduits are treated with a surface chemistry modifying process prior to being embedded in the sealing members. The surface chemistry modifying process may comprise corona treatment or other processes which break molecular bonds at the surface of the polymeric hollow conduits. Other examples of surface treatment process include plasma or flame processes and chemical etching.

In accordance with another embodiment of the present invention, a method is provided for producing a blood heat exchanger which utilizes a plurality of hollow elongated polymeric conduits for conveying blood. The conduits are treated with a surface chemistry modifying process such as corona, plasma, flame or chemical etching. The conduits are bundled and then the ends of the bundled conduits are embedded in a sealing compound. The surface chemistry modifying process facilitates good adhesion between the sealing compound and the bundles. The ends of the sealed conduit bundle are then cut to expose the open ends of the hollow conduits. The conduit bundle is inserted into a heat transfer fluid chamber wherein the sealing compound prevents fluids from passing from the heat transfer fluid chamber to the ends of the conduits.

The invention affords a number of distinct advantages. The surface chemistry modifying process makes possible a secure and reliable bond between the sealing compound and the conduits. This ensures that fluids from the heat exchange transfer fluid chamber cannot pass through the sealing compound and reach the blood at the ends of the conduits. By providing improved sealing of the polymeric conduits, the conduits may be made extremely small to take full advantage of the polymeric material. With smaller microconduits, many more micro-conduit fibers can be used in the same volume thereby increasing the overall surface area of the blood heat exchanger. The greater number of microconduit fibers also minimizes the effect of any fibers that may become plugged, avoiding any significant alteration of the flow dynamics of the heat exchanger by providing a gradual degradation thereby. Furthermore, the small microconduits have very thin walls which further improves heat transfer. Thus, the invention advantageously provides a blood heat exchanger with markedly improved heat exchange characteristics. Furthermore, the polymeric material of the conduits and the material of the sealing compound are biocompatible materials which do not pose any toxicity problems when in contact with blood.

Another advantage of the invention includes its low cost, since the micro-conduit can be made from inexpensive materials. The micro-conduit is also beneficial for use in the manufacturing process, since it is lightweight, flexible, easily cut, and largely transparent.

BRIEF DESCRIPTION OF THE DRAWINGS

The nature, objects and advantages of the invention will become more apparent to those skilled in the art after considering the following detailed description in connection with the accompanying drawings, in which like reference numerals designate like parts throughout, wherein.

DETAILED DESCRIPTION OF THE PREFERRED EMBODIMENTS

The present invention concerns a blood heat exchanger which employs a polymeric micro-conduit to carry blood while a heat transfer fluid passes around the micro-conduits to permit temperature control of the blood. The invention provides an effective and reliable technique for sealing the ends of the micro-conduits to prevent any contamination of blood by the heat transfer fluid.

STRUCTURE

Figure 1:
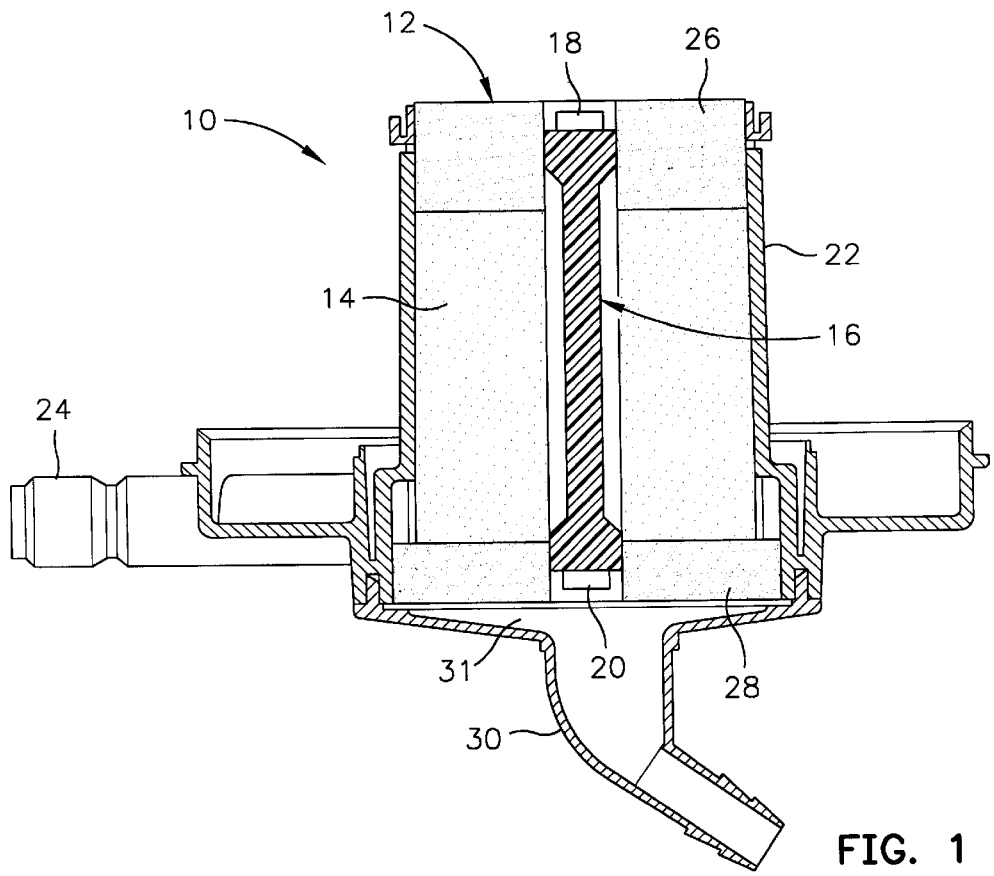
FIG. 1 is a vertical sectional view of a blood heat exchanger apparatus in accordance with the invention.

FIG. 1 depicts an example of a heat exchanger of the present invention. The heat exchanger 10 includes a generally cylindrical heat exchange core 12 which is made from a micro-conduit wrapping material 14 wound about a central spindle 16. The spindle has first and second ends 18, 20. The individual fibers of the wrapping material 14 (shown in more detail in FIGS. 2 and 3) are cut to provide substantially flat end surfaces proximate the first and second ends 18, 20 of the spindle 16. The core 12 may include, for example, about five thousand four-hundred individual fibers. A rigid cylindrical shell 22 encloses the core 12 and spindle 16. The shell 22 includes an inlet 24 and an outlet (not shown) to facilitate the flow of a heat transfer fluid through the shell 22 and around the micro-conduit wrapping material 14 inside the shell 22. In a preferred embodiment the heat exchange medium is water which has adequate heat exchange properties while also being relatively biocompatible as compared to other commonly used heat exchange mediums.

The core 12 includes an upper seal 26 and a lower seal 28. The upper and lower seals 26, 28 comprise a layer of potting compound sealingly applied between the individual fibers of the micro-conduit wrapping material 14 approximate the spindles first and second ends 18, 20. In the preferred embodiment, the potting compound comprises a urethane material however other materials of suitable utility and biocompatability may be utilized. The upper and lower seals 26, 28 are applied in a manner described in more detail below. Importantly, the seals 26, 28 provide a tight and reliable isolation between the heat exchange medium entering inlet 24 and the blood passing through the individual fibers of the micro-conduit wrapping material 14.

Figure 1A:
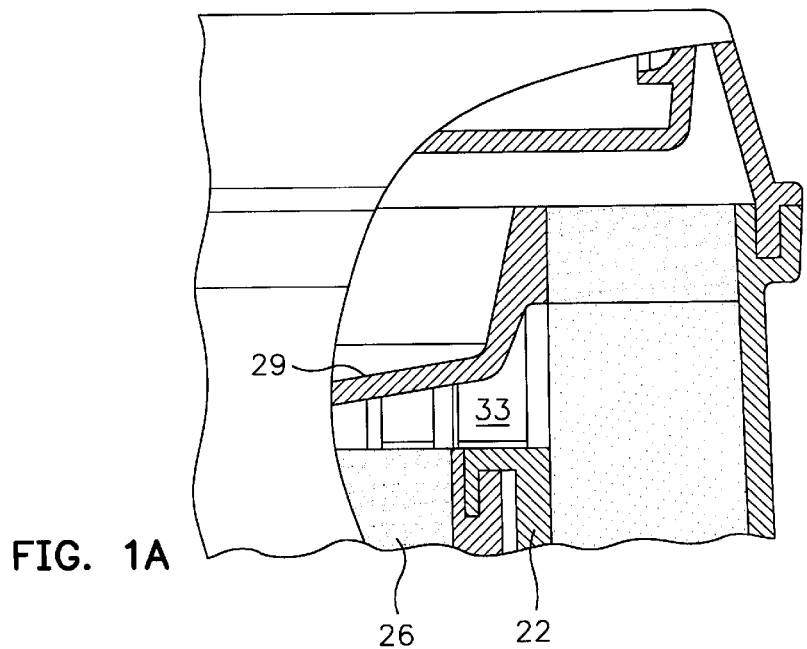
FIG. 1A is an enlarged vertical sectional view of a portion of the blood oxygenator employing the heat exchanger apparatus shown in FIG. 1.

Referring now to both FIGS. 1 and 1A, the core 12 is enclosed within the shell 22 by an upper blood transition manifold 29, forming outlet chamber 33 and a lower blood inlet manifold 30 forming inlet chamber 31. Further details of the heat exchanger 10 are described in co-pending U.S. patent application Ser. No. 08/585,322 filed on even date herewith, entitled Compact Membrane-Type Blood Oxygenator With Concentric Heat Exchanger and U.S. patent application Ser. No. 08/584,275 filed on even date herewith, entitled Blood Heat Exchange System Employing Micro-Conduit. The entire disclosures of the aforementioned patent applications are specifically incorporated herein by reference. These applications are assigned to Medtronic, Inc. of Minneapolis, Minn. U.S.A.

Figure 2:
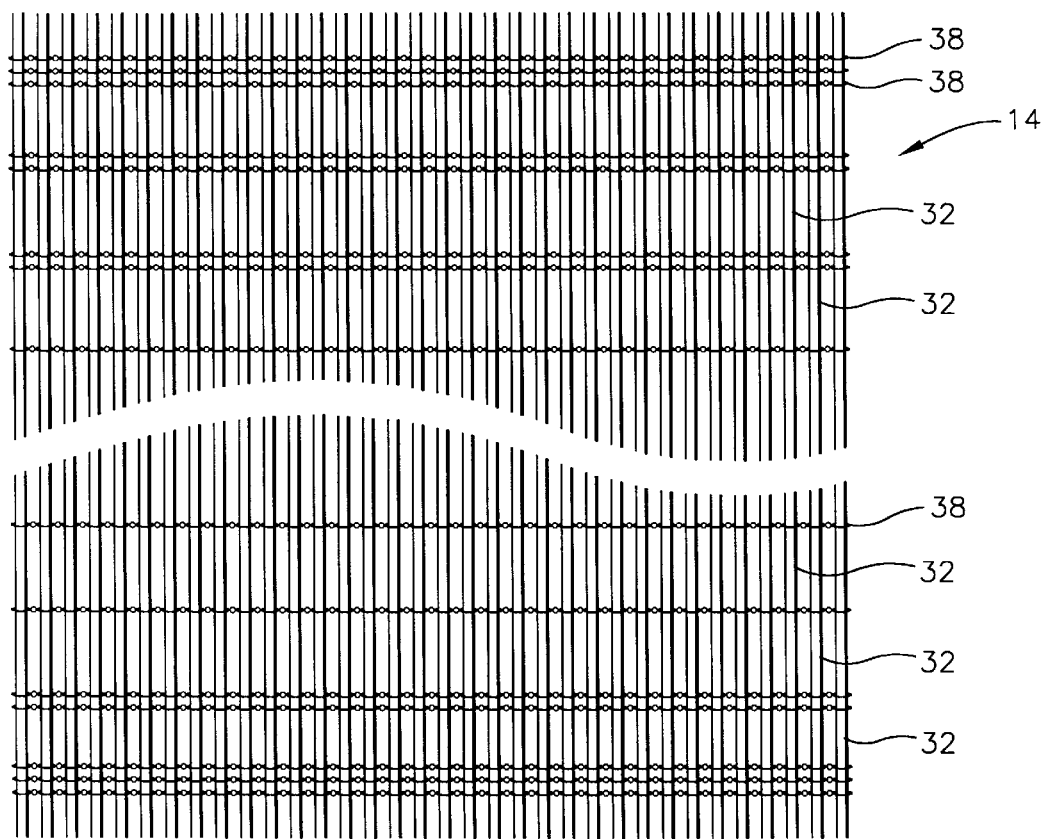
FIG. 2 is a greatly enlarged plan view of a micro-conduit wrapping material in accordance with the invention.
Figure 3:
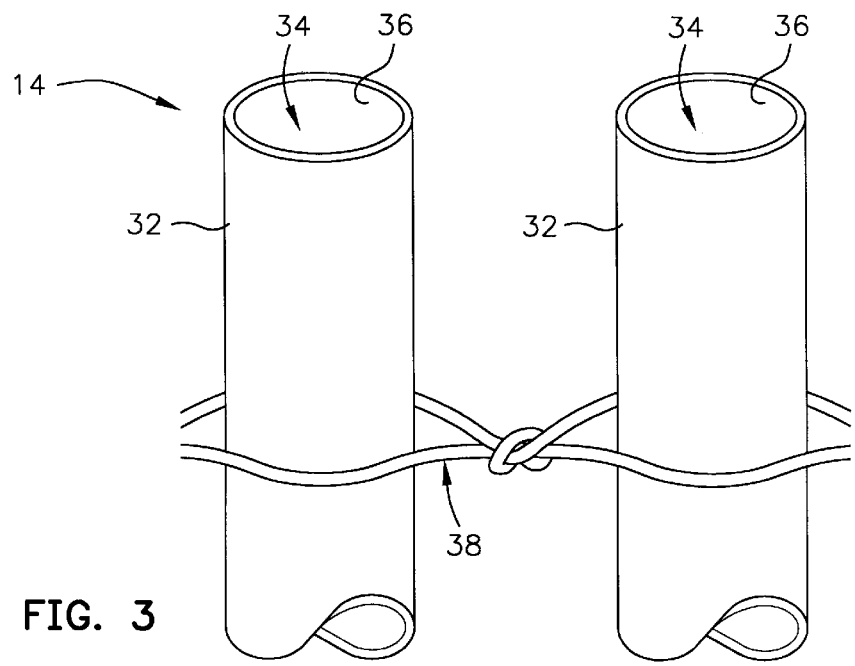
FIG. 3 is further enlarged perspective view of a section of micro-conduit wrapping material of FIG. 2.

FIG. 2 depicts the micro-conduit wrapping material 14 prior to wrapping into the core 12 shown in FIG. 1. The micro conduit wrapping material 14 comprises a plurality of small fibers 32. Each fiber 32 is hollow, with a cross-sectional shape preferably being rounded, or alternatively triangular, rectangular or other appropriate shape. As shown in FIG. 3, since the fibers 32 are hollow, each fiber 32 has defined therein an inner channel 34 having an inner surface 36. In a preferred embodiment, the fibers outer diameter is about five hundred and seventy-five microns, while the inner channel 34 has a diameter of about four-hundred and twenty-eight microns. As an example, the fibers 32 may be about ten centimeters long. However, a wide range of fiber lengths may be used, depending upon the requirements of a particular application for the blood heat exchanger.

The fibers 32 are preferably made from a plastic material such as polypropylene, polyethylene, a different polymeric substance, or other material that is inexpensive, pharmacologically safe, lightweight, easily cut and flexible. The material of the fibers 32 should also be easily formed into fibers with sufficiently small inner and outer dimensions.

The micro-conduit wrapping material 14 includes a thin flexible interconnect 38 that maintains the fibers 32 at predetermined spacing in substantially parallel alignment with each other. In the illustrated embodiment, the interconnect 38 comprises substantially parallel, flexible, non-active, multifilament threads that are woven or knotted to hold the fibers about 0.5 millimeters apart generally parallel to each other. The wrapping material 14 aides in positioning the fibers 32 during surface treatment and construction of the blood heat exchanger as discussed in more detail below.

The wrapping material 14 is preferably made of a commercially available product from Mitsubishi Rayon Company Limited sold under the designation HFE430-1 Hollow Fiber. The fibers of this product are made of polyethylene. Similar wrapping material is also commercially available from Hoechst Celanese Corp. under the designation Heat Exchanger Fiber Mat, which uses polypropylene fibers.

FABRICATION

An important feature of the present invention is the reliable seal between the heat transfer fluid and the blood provided by the seals 26 and 28. As learned by the present inventors, while the polymeric material used for the fibers 32 have many advantages, difficulties arise in attempting to seal the heat transfer fluid and blood interface. The potting material used for seals 26 and 28 must adequately surround each individual fiber 32 and adhere completely to avoid leaks. Furthermore, the seal must be maintained indefinitely and cannot delaminate over time or when subjected to various environmental conditions. This issue is critical since no amount of leakage of the heat transfer fluid into the patient's blood is acceptable. This problem has been resolved by the present inventors by utilizing a surface treatment process which alters the surface chemistry of the polymer based micro-conduit fiber 32 in a manner which improves the adhesion of the sealant of the urethane sealant used for the seals 26 and 28 to the fibers 32.

Polymeric materials, such as polyolefins including polypropylene and polyethylene, have a surface chemistry which make it difficult to achieve the necessary seal by sealants 26 and 28. The problem is that the surfaces are inactive, that is, they have a very low surface energy. This is because the molecules are long and there are no active chemical bonding sights available. This results in a low critical surface tension (about 30 Dynes/$Cm^2$) which makes the surface less wettable. Wettability is important because if an adhesive does not wet the fiber then the adhesive is effectively not bonding to the fiber because it is not really touching the fiber. In particular, the fiber 32 surface is quite rough on a microscopic level. If the surface is not wettable the bonding liquid, such as urethane, does not penetrate the grooves in the surface. Consequently, there is less contact area between the bonding liquid and the fiber surface, and leaking can result.

In accordance with the present invention the fiber surface is treated with a surface chemistry altering process which reduces the critical surface tension and thereby makes the surface more wettable. This will allow the bonding liquid to be drawn into and penetrate the microscopic grooves in the fiber surface. As a result, there is a larger bonded surface area and the strength as the bond is increased. Therefore, the likelihood of leaking is significantly reduced. In accordance with the present invention a high energy is applied to the surface of the fiber 32 which breaks molecular bonds. This causes the molecules in the fiber to become unstable, thus creating new molecular ends which are reactive with other molecules, or with each other. The surface will then have a higher surface energy and a lower critical surface tension, making it more wettable.

The way this process works on a molecular level is that a high energy source in the presence of air, such as produced by a corona discharge machine, will modify the oxygen in the air into a variety of reactive species. The most stable of these is ozone, which is the unstable form of oxygen that contains three atoms of oxygen. Ozone has a variety of pathways by which it can decompose and most of these produce other reactive molecules that include oxygen. These molecules, in the presence of organic materials like polymers, will react with them. In the case of fibers 32 the reaction will work into the outside surface first. These reactions could take two forms, one would be that it attacks the pendant group on the polymer chain, which is the methyl group in polypropylene. That is, the ozone or other reactive oxygen species is capable of attacking these pendant groups and knocking off hydrogen or cleaving off the pendant group altogether. Alternatively, the oxygen radical which forms on the decomposition of ozone could also cleave the main chain of the absence of a double bond. In sum, the surface is attacked at a variety of points and changes its nature so that it makes the surface more reactive and decreases the contact angle.

Figure 4:
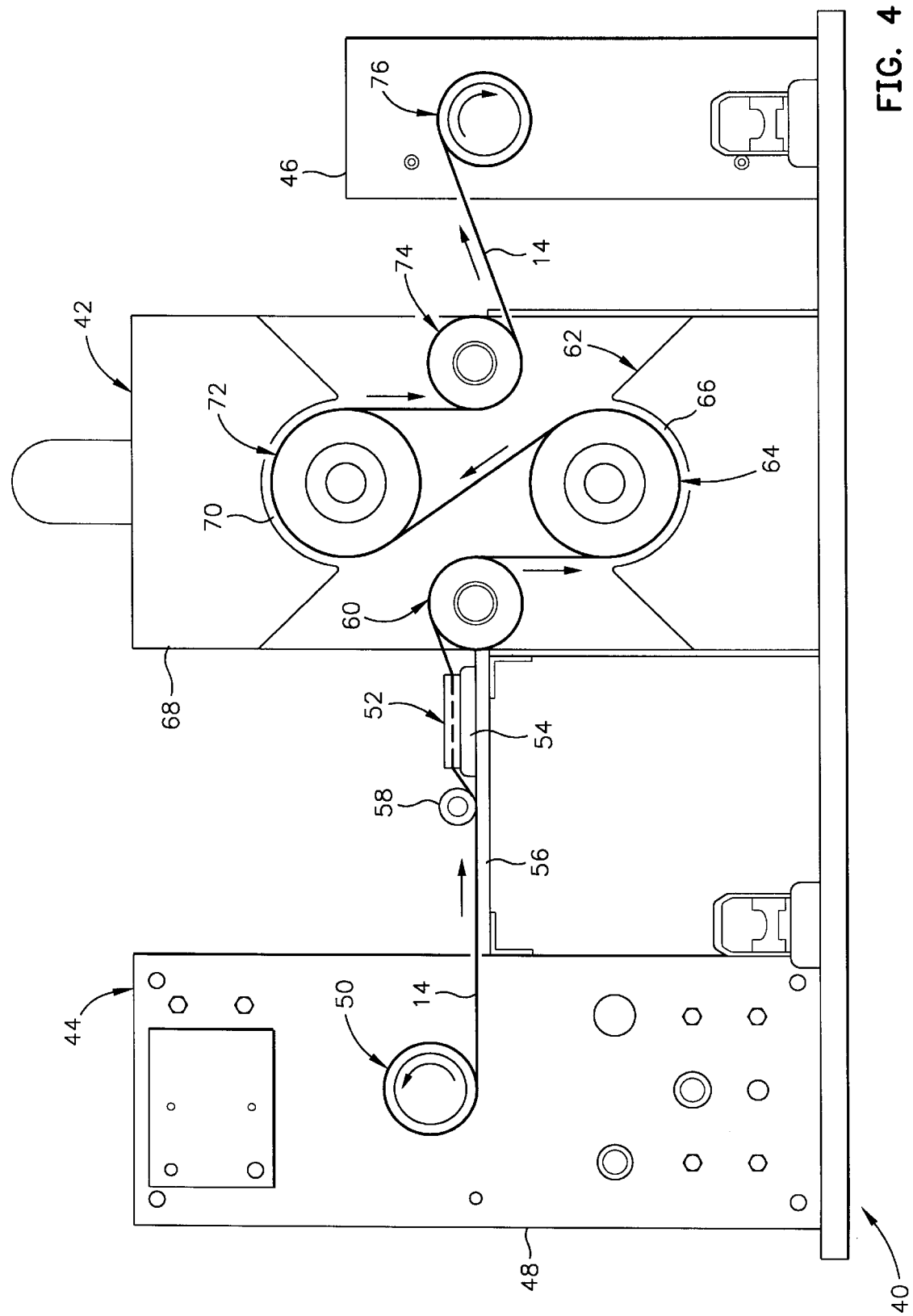
FIG. 4 is a schematic view of a corona treatment apparatus used in treating the micro-conduit wrapping material in accordance with a preferred embodiment of the present invention.

In order to achieve this alteration of the surface chemistry of the micro-conduit wrapping material 14, a surface treatment process in accordance with the preferred embodiment of the present invention is utilized which is illustrated in FIG. 4. A corona discharge system 40 is employed which generates a high voltage electrical arc. By exposing the fiber 32 to this arc the desired alteration of surface chemistry is achieved. Other techniques may also be employed to achieve the same result such as an exposure to plasma or flame or chemical etching of the fiber 32. Corona discharge is preferred because it is easy to control, is not expensive, operates in ordinary atmosphere and doesn't utilize chemicals which are not bio-compatible.

In particular, the corona discharge system 40 (FIG. 4), utilizes a corona treating apparatus 42 known as the Cantilever Corona Treating System commercially available from Corotec Corporation of Farmington, Conn., U.S.A. This Corotec corona machine does not generate extremely high levels of heat on the micro-conduit wrapping material 14. This is important since the interconnect thread 38 can be melted by some corona machines which generate higher levels of heat. The standard Corotec corona treating apparatus is modified so that it has two corona treating heads as shown in the corona treatment apparatus 42 in FIG. 4. Two treatment heads are desirable because treatment of the micro-conduit wrapping material 14 from one side only might not result in treatment of the back side of the fiber.

The corona treatment 40 (FIG. 4) also includes an unwinder unit 44 and a rewinder 46 unit for conveying the micro-conduit wrapping material 14 into and out of the corona treatmnet apparatus 42. The unwinder unit 44 includes a frame 48 which carries an unwinder spool 50 around which the micro-conduit wrapping material 14 is wound. A guider unit 52 carries the micro-conduit wrapping material 14 and guides it in the proper position into the corona treatment apparatus 42. The guider unit 52 includes a guider 54 that contains a channel that positions the micro-conduit wrapping material in the desired lateral and vertical position for entry into the corona treatment apparatus 42. The guider 54 rests on a shelf 56 and an idler pulley 58 creates the desired tension on the micro-conduit wrapping material 14 before it enters the guider 54. It is important that this tension be minimal to ensure that the mat is not stretched or distorted.

After leaving the guider unit 52 (FIG. 4) the micro-conduit wrapping material 14 passes around an idler pulley 60 in the corona treatment apparatus 42. The horizontal motion of the micro-conduit wrapping material is then translated into a vertically downward path around the idler pulley 60 as it enters a first corona treatment unit 62. Electrode/roller 64 carries the micro-conduit wrapping material 14 into and out of a semi-circular arc gap 66 wherein the fibers 32 are exposed on one side to an arc (not shown) generated by a high voltage electrical potential. The arc exists within the entire arc gap 66, that is, about one hundred and eighty degrees around the electrode/roller 64. This has the effect of altering the surface chemistry of the fibers 32 as described above. The arc is generated by a high-frequency (such as 30 khz) high voltage power source applied to the roller/electrode 64.

Since one side of the fibers are in contact with roller/electrode 64, it is advantageous to expose the opposite side of the fibers 32. This is done by passing the micro-conduit wrapping material 14 through a second corona treatment unit 68 by means of a second corona treatment roller/electrode 72 which causes the fibers to pass a second corona treatment cavity 70 where they are exposed to a second arc on the opposite sides of the fibers. After the second corona treatment, the micro-conduit wrapping material 14 passes around idler pulley 74 where it then is wound up by rewinder unit 46 around rewinder spool 76.

It should be noted that the exposure to the corona treatment can be controlled by the power density and the speed with which the micro-conduit wrapping material passes through the corona treatment apparatus 42. Adequate corona treatment has been achieved by setting the Corotec machine described above at its maximum power density setting. This machine will automatically adjust the strength of the arc to yield a constant power density regardless of the speed at which the micro-conduit wrapping material passes through the Corona treatment system. As a result the surface tension of the fibers will be about 38 or greater Dynes/cm$^2$, significantly above the surface tension of about 30 or less Dynes/cm$^2$ before treatment. Once treated, it should be noted that the bonds which have been broken in the surface chemistry of the polymeric fibers 32 will reattach themselves over time. Thus, the fibers should be bonded to the potting material of seals 26 and 28 relatively soon. For example, it has been observed that the corona treatment is still effective after the course of a few weeks, but may be reduced after several months have passed.

Figure 5:
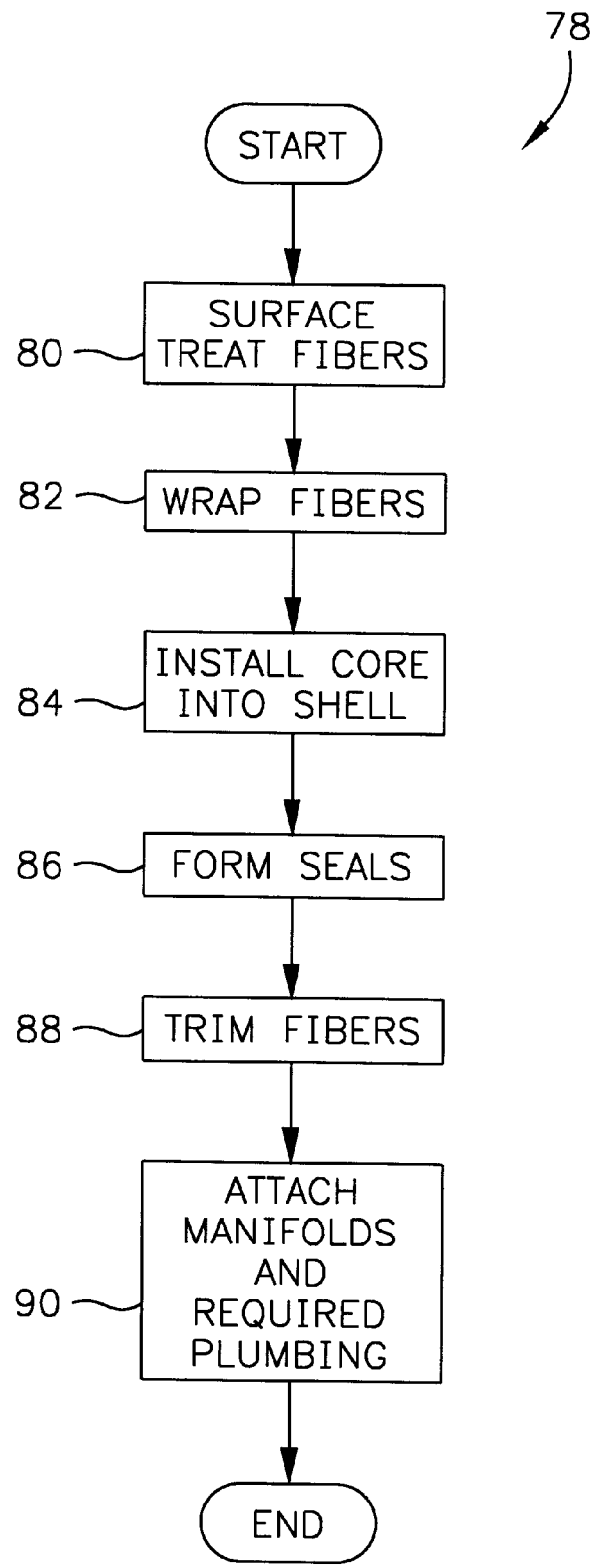
FIG. 5 is a flow chart of a sequence of steps used in fabricating a heat exchanger apparatus in accordance with the invention.

Referring now to FIG. 5, a sequence 78 for manufacturing a blood heat exchanger in accordance with one example of the invention is illustrated. First, in task 80, the surface of the fibers 32 are treated in accordance with one of the above described surface treatment techniques such as the corona treatment described in connection with FIG. 4. Next, in task 82, the micro-conduit wrapping material 14 is wrapped around the spindle 16, preferably without any substantial tension on the wrapping material. After task 82 the shell 22 is installed over the core 12 in task 84.

In task 86, the upper and lower seals 26, 28 are formed. In the preferred embodiment a urethane potting compound is injected between the fibers 32 to substantially seal the spaces between the fibers. This is done by putting the ends of the fibers in potting cups and inserting the core 18 into a centrifuge and spinning it while urethane from a reservoir fills the cups. The high G forces of the spinning process forces the urethane around the exterior of the fibers. The thickness of the upper and lower seals 26, 28 is determined by the amount of urethane which is used during the potting process. Before task 80, the ends of the fibers 32 may be sealed to prevent the potting compound from entering therein.

Importantly, due to the prior surface treatment of the fibers in task 80, excellent adhesion between the fibers 32 and the potting compound, such as urethane is achieved. Consequently, the seals 26 and 28 are free of leaking or delamination and will reliably isolate and seal the heat transfer fluid passing around the outside of the fibers from the blood entering and leaving the ends of the fibers. In the preferred embodiment the potting material is a bio-compatible urethane commercially available under the name BIOTHANE from CasChem Corporation of Bayonne, N.J., U.S.A. This is a particular formulation of urethane which has as its primary components Polycin and Vorite. Other kinds of urethane may also be suitable in some applications, as well as non-urethane potting materials such as epoxy and silicone.

Next, the fibers 32 are trimmed proximate the first and second ends 18, 20 of the spindle 16 as shown in task 88. Preferably, the trimmed fibers 32 form uniform flat upper and lower surfaces of the core 12. This trimming is preferably a two-stage process in which a rough cut is initially made with a rotary blade and then the ends are trimrned with a microtome. Finally, in task 90, the manifolds such as 30 are attached to the shell 22. Also, in task 90 hoses and other plumbing lines are attached to the heat exchanger 10 as needed for transportation of heat exchange fluid, blood, priming solution, and other media as appropriate.

OPERATION

Generally, the heat exchanger 10 serves to regulate the temperature during a medical procedure such as open-heart surgery. Heat exchanger 10 also may be advantageously incorporated into a blood oxygenator such as disclosed in the aforementioned U.S. patent application entitled "Compact Membrane-Type Blood Oxygenator With Concentric Heat Exchanger" Ser. No. 08/585,322. Referring to FIGS. 1–3, a heat transfer fluid such as water flows into the shell 22 through the inlet 24 during the medical procedure. While in the shell 22, the heat transfer fluid passes between and around the exterior of the fibers 32 in the core 12, preferably flowing in a direction opposite to the of blood. This counterflow is achieved using a flow channel, (not illustrated) for the water which flows from inlet 24 to the top of the shell 22 where the water exists and flows downwardly. Due to the large number of fibers 32 and their small size and thin walls, there is substantial area of surface contact and heat exchange between the heat exchange fluid and the blood inside the fibers 32. During ongoing operation of the heat exchanger 10, a patient's blood which flows into inlet manifold 30 and chamber 31 through the fibers 32 of the core 12 and exits through the upper end of the fibers past seal 26 through a transition manifold 29 and outlet chamber 33. As a result, the temperature of the blood flowing through the core may be easily regulated by a heat exchange fluid temperature controlling unit (not shown) due to the high degree of thermal contact between the blood and the heat exchange medium as well as the relatively high thermal conductivity of the thin wall fibers 32.

Before directing any blood through the fibers 32 it is important to prime the fibers' to thoroughly wet the fibers inner surfaces and thereby prevent formation of liquid or gas bubbles inside fibers. This priming may be advantageously employed utilizing the techniques taught in the aforementioned U.S. patent application entitled "Blood Heat Exchange System Employing Micro-conduit", Ser. No. 08/584,275.

TESTING

An exemplary embodiment of the heat exchanger 10 was constructed in accordance with the invention for testing and evaluation. The test-model heat exchanger included a core 12 of five-thousand four-hundred fibers 32 each having a length of about three and four tenths inches. No leaking of either heat exchange fluid or blood passing the upper and lower seals 26, 28 was detected. To roughly gauge the performance of the test-model heat exchanger, a blood flow of six liters/minute was maintained through the fibers 32 after priming. Simultaneously a water flow of fifteen liters/minute was maintained through the core. The incoming blood temperature was thirty degrees C. and the incoming water temperature was forty degrees C. The blood's hemoglobin rating was twelve grams per deciliter.

The temperature of the outgoing blood and water was measured and averaged, based upon several different experiments conducted under the conditions listed above. Based upon this information, a "performance factor" of 0.65 was computed for the test-model heat exchanger 10 using the formula of equation 1 below.

$$\text{performance factor} = \frac{B_{out} - B_{in}}{W_{in} - B_{in}} \quad [1]$$

where: $B_{in}$=the temperature of the incoming blood, set at 30° Celsius;

$W_{in}$=the temperature of the incoming water, set at 40° Celsius; and $B_{out}$=the temperature of the outgoing blood.

While there have been shown what are been presently considered to be the preferred embodiments of the invention, it will be apparent to those skilled in the art that various changes and modifications can be made herein without departing from the scope of the invention as defined by the appended claims.

What is claimed is:

1. A blood heat exchange system comprising:

a plurality of hollow conduits for conveying blood therethrough;

heat transfer fluid flow path for conveying a heat transfer fluid around the outside surfaces of the hollow conduits;

an inlet chamber for directing blood into the hollow conduits and outlet chamber for receiving blood leaving the hollow conduits, the hollow conduits being arranged in a bundle, wherein each hollow conduit has a first end terminating in the inlet chamber and a second end terminating in the outlet chamber;

each end of the conduit bundle being embedded in one of two sealing members which seals the inlet and output chambers respectively from the heat transfer fluid flow path disposed therebetween; and the hollow conduits being composed of a plastic material having at least the end portions treated with a surface chemistry modifying process prior to being embedded in the sealing members for providing improved sealing of the conduits, where the hollow conduits have a surface tension of at least about 38 Dynes/cm$^2$ after the surface chemistry modification process.

2. The heat exchange system according to claim 1 wherein the hollow conduits comprise a mat of hollow conduits aligned side-by-side and attached by a woven fiber.

3. The heat exchange system according to claim 2 wherein the mat is wound around a central spool forming the hollow conduits into a cylindrical shaped bundle.

4. The heat exchange system according to claim 1 wherein the hollow conduits are made of polyethylene.

5. The heat exchanger according to claim 1 wherein the hollow conduits are made of polypropylene.

6. The heat exchanger according to claim 1 wherein each hollow conduits have a round cross-section.

7. The heat exchanger according to claim 1 wherein each sealing member is made of a urethane potting compound.

8. The heat exchanger according to claim 1 wherein the surface chemistry altering process is a corona discharge process.

9. The system according to claim 1 wherein the surface chemistry altering process is a plasma process.

10. A method of producing a blood heat exchanger comprising the steps of:

providing a plurality of hollow elongated polymeric conduits;

treating at least the outside surfaces of the end portions of the conduits with a surface chemistry modifying process that enhances the adhesion between a sealing compound and the conduits;

bundling the conduits;

inserting the conduit bundle into a heat transfer fluid chamber;

embedding the end portions of the bundled conduits in a sealing compound, while spinning the conduits in a centrifuge wherein the surface chemistry modifying process facilitates the adhesion between the sealing compound and the conduits and the sealing compound prevents fluids from passing from the heat transfer fluid chamber to the ends of the conduits; and cutting the ends of the sealed conduit bundle to expose the open ends of the hollow conduits.

11. The method of claim 10 further comprising the step of attaching to the blood heat exchanger a blood inlet chamber for allowing blood to flow from the chamber into one end of each of the conduits.

12. The method of claim 10 wherein the step of treating comprises the step of exposing the conduits to a corona process.

13. The method of claim 10 wherein the step of bundling the conduits forms the conduits into a generally cylindrical core.

14. The method of claim 10 wherein the step of bundling the conduits includes attaching them together by a woven fiber to form a mat and the step of bundling the conduits comprises the step of winding the mat around a spool.

15. The method of claim 10 and further comprising the step of sealing the ends of the conduits prior to the step of embedding wherein the sealing compound is prevented from entering the conduits.

* * * * *